(12) United States Patent
Woodburn, Sr. et al.

(10) Patent No.: US 11,090,149 B2
(45) Date of Patent: Aug. 17, 2021

(54) INFLATABLE ORBITAL IMPLANT FOR REPOSITIONING AN EYEBALL, AND RELATED METHODS

(71) Applicant: DePuy Synthes Products, Inc., Raynham, MA (US)

(72) Inventors: William N. Woodburn, Sr., Mickleton, NJ (US); Peter Van Citters, Phoenixville, PA (US); Michael Brace, Lansdale, PA (US); Veronika Legkobitova, Philadelphia, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 170 days.

(21) Appl. No.: 16/146,418

(22) Filed: Sep. 28, 2018

(65) Prior Publication Data

US 2020/0100894 A1    Apr. 2, 2020

(51) Int. Cl.
*A61F 2/14* (2006.01)
*A61F 9/007* (2006.01)
*A61F 2/28* (2006.01)

(52) U.S. Cl.
CPC .............. *A61F 2/141* (2013.01); *A61F 9/007* (2013.01); *A61F 2002/2878* (2013.01); *A61F 2250/0003* (2013.01)

(58) Field of Classification Search
CPC .... A61F 2/141; A61F 2002/2878; A61F 2/14; A61F 2250/0003; A61F 2250/0004; A61F 9/0017; A61B 17/8855; A61B 17/025
See application file for complete search history.

(56) References Cited

U.S. PATENT DOCUMENTS

| | | | |
|---|---|---|---|
| 4,863,474 A | 9/1989 | Brown et al. |
| 5,139,497 A | 8/1992 | Tilghman et al. |
| 5,250,048 A | 10/1993 | Gundolf |
| 5,383,931 A | 1/1995 | Hehli et al. |
| 5,468,242 A | 11/1995 | Reisberg |
| 5,546,784 A | 8/1996 | Haas et al. |
| 5,766,176 A | 6/1998 | Duncan |
| 5,814,048 A | 9/1998 | Morgan |
| 6,008,430 A | 12/1999 | White |
| 6,053,026 A | 4/2000 | Nardiello et al. |

(Continued)

FOREIGN PATENT DOCUMENTS

| | | | | |
|---|---|---|---|---|
| AT | 384945 B | * | 1/1988 | ............ A61B 17/24 |
| DE | 3425002 A1 | | 1/1985 | |

(Continued)

*Primary Examiner* — David H Willse
*Assistant Examiner* — Javier G Blanco
(74) *Attorney, Agent, or Firm* — BakerHostetler

(57) ABSTRACT

An orbital implant includes a bladder configured to be implanted between an orbit and an eyeball of a patient. The bladder defines at least one port and at least one compartment in fluid communication with each other. The at least one compartment defines an interior volume and is configured to hold a fill material so as to be adjustable responsive to injection of fill material into the at least one compartment through the at least one port as well as removal of fill material from the at least one compartment through the at least one port. Adjustment of the interior volume is configured to reposition the eyeball.

2 Claims, 7 Drawing Sheets

(56) References Cited

U.S. PATENT DOCUMENTS

| | | | |
|---|---|---|---|
| 6,419,698 B1* | 7/2002 | Finger | A61F 2/141 |
| | | | 623/6.41 |
| 7,655,047 B2 | 2/2010 | Swords | |
| 7,662,155 B2 | 2/2010 | Metzger et al. | |
| 8,281,638 B2 | 10/2012 | Metzger | |
| 2006/0116682 A1 | 6/2006 | Longo | |
| 2007/0156146 A1* | 7/2007 | Metzger | A61F 2/2875 |
| | | | 606/86 A |
| 2007/0270634 A1* | 11/2007 | Elahi | A61L 31/14 |
| | | | 600/37 |

FOREIGN PATENT DOCUMENTS

| | | |
|---|---|---|
| WO | 01/72246 A1 | 10/2001 |
| WO | 02/92882 A1 | 11/2002 |
| WO | 03/07831 A1 | 1/2003 |

* cited by examiner

INFLATABLE ORBITAL IMPLANT FOR REPOSITIONING AN EYEBALL, AND RELATED METHODS

TECHNICAL FIELD

The present disclosure relates generally to orbital implants, and in particular relates to an inflatable orbital implant that can reposition an eyeball of a patient via adjustment to an inflation level of the implant.

BACKGROUND

Fractures in the orbita can be treated with plating technology, such as grid-like plates (also referred to as "meshes") implanted so as to overlay and/or integrate with a defective portion of the orbital structure, such as in an orbital reconstruction procedure. Such plates or "meshes" are available in different patterns and strengths and are commonly designed to be flat for distribution purposes, and can also be pre-shaped or formed to the orbital anatomy of a particular patient. However, even following a successful orbital reconstruction, various conditions can cause the eyeball of the reconstructed orbit to become subsequently misaligned with the other eyeball, such tissue necrosis, scarring, and swelling, for example. Such conditions can result, for example, in the eyeball of the reconstructed orbit dropping vertically relative to the other, which can result in diplopia (i.e., double vision). Such misalignment can worsen progressively over time.

SUMMARY

According to an embodiment of the present disclosure, an implant includes a bladder configured to be implanted between an orbit and an eyeball of a patient. The bladder defines at least one port and at least one compartment in fluid communication with each other. The at least one compartment defines an interior volume and is configured to hold a fill material so as to be adjustable responsive to injection of fill material into the at least one compartment through the at least one port as well as removal of fill material from the at least one compartment through the at least one port. Adjustment of the interior volume is configured to reposition the eyeball.

According to another embodiment of the present disclosure, an orbital implantation system includes a bladder configured to be anchored within an orbit and adjacent an eyeball of a patient. The bladder defines a port and a compartment in fluid communication with each other. The compartment defines an interior volume that is adjustable responsive to 1) injection of fill material into the internal volume through the port, and 2) removal of fill material from the interior volume through the port. The adjustment of the interior volume is configured to reposition the eyeball along a direction. The system includes a reservoir of fill material located externally of the patient and an injection device in fluid communication with the reservoir and configured to communicate a quantity of the fill material though the port so as to adjust the interior volume of the compartment.

According to yet another embodiment of the present disclosure, a method of repositioning an eyeball of a patient includes adjusting an inflation level of a bladder implanted between the eyeball and a portion of a respective orbit of the patient. The adjusting step comprises communicating a fill material through a port in fluid communication with an internal volume of the bladder.

BRIEF DESCRIPTION OF THE DRAWINGS

The foregoing summary, as well as the following detailed description of illustrative embodiments of the implant of the present application, will be better understood when read in conjunction with the appended drawings. For the purposes of illustrating the implant(s) of the present application, there is shown in the drawings illustrative embodiments. It should be understood, however, that the application is not limited to the precise arrangements and instrumentalities shown. In the drawings.

DETAILED DESCRIPTION OF ILLUSTRATIVE EMBODIMENTS

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

The term "plurality," as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

The embodiments disclosed herein pertain to an inflatable orbital implant configured to reposition an eyeball (i.e., the "globe"), such as following an orbital floor reconstruction procedure, by way of a non-limiting example. Orbital floor reconstructions are challenging procedures, particularly with respect to restoring the anatomical alignment of the associated eyeball. As mentioned above, misalignment of one eyeball with respect to the other can result in diplopia (i.e., double vision), which can occur following an orbital floor reconstruction if certain post-operative conditions occur, such as necrosis of orbital tissue, swelling, and the development of scar tissue, by way of non-limiting examples. The implants described below include one or more bladders (which can also be referred to as "balloons") configured to be disposed within an orbit and engage the eyeball, such that adjustment of an inflation level of the bladder(s) repositions the eyeball as needed to restore its alignment.

Figure 1:
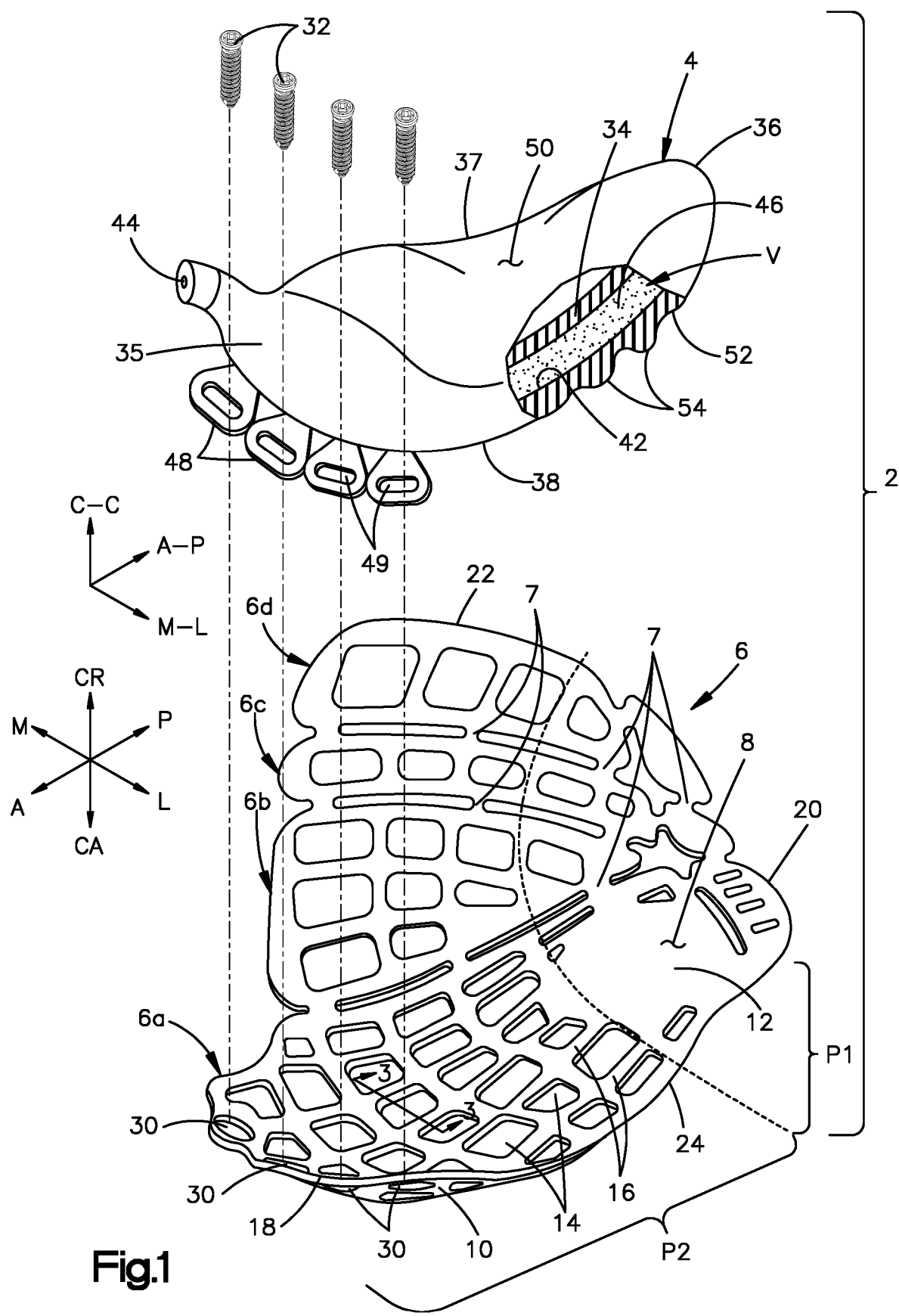
FIG. 1 is an exploded perspective view of an inflatable orbital implant that includes a plate and an inflatable bladder, according to an embodiment of the present disclosure.

Referring to FIG. 1, an orbital implant 2 includes a bladder 4 that can be carried, or otherwise supported by, a support plate 6, which defines a first surface 8 that faces the bladder 4 and an opposed second surface 10 that is configured to face the underlying anatomical structure, particularly one or more orbital bones, of a patient. Thus, the first surface 8 is also referred to herein as the "interior surface" of the support plate 6, while the second surface 10 is also referred to herein as the "exterior surface" of the support plate 6. The support plate 6 can also be referred to herein as simply the "plate." The plate 6 has a body 12 composed of a biocompatible material, such as, by way of non-limiting examples, a metal, such as stainless steel, titanium or a titanium alloy, or a polymeric material, such as polyethylene or polyetheretherketone (PEEK). The plate body 12 can be in the form of a mesh structure that defines a plurality of apertures 14 extending from the interior surface 8 to the exterior surface 10 (and thus also extending from the exterior surface 10 to the interior surface 8) and a plurality of plate segments 16 located between the apertures 14. In such embodiments, the support plate 6 can also be referred to as a "support mesh." In other embodiments, however, the plate 6 can be a continuous layer of material (including any of those non-limiting materials described above) that is devoid of apertures 14. One non-limiting example of such a plate 6 is a thin, continuous layer of polyethylene that can be pre-shaped to the geometry of the orbital floor, which can provide the layer with a shape that can be characterized as being similar to that of a potato chip. It is to be appreciated that other plate 6 configurations are within the scope of the present disclosure.

The plate 6 can extend between a first or anterior end 18 and a second or posterior end 20 that are spaced from each other generally along a first direction, which can also be referred to herein as the anterior-posterior direction A-P. The plate 6 can define an anterior region A1 and a posterior region P1 spaced from each other along the anterior-posterior direction A-P. The anterior region A1 can extend from the anterior end 18 toward the posterior region P1 in a posterior direction P. The posterior region P1 can extend from the posterior end 20 toward the anterior region A1 in an anterior direction A that is opposite the posterior direction P. It is to be appreciated that the anterior direction A and the posterior direction P are each mono-directional components of the anterior-posterior direction A-P, which is bi-directional.

The plate 6 can extend between a third or medial end 22 and a fourth or lateral end 24 that are spaced from each other generally along a second direction, which can also be referred to herein as the medial-lateral direction M-L. It is to be appreciated that the medial-lateral direction M-L is substantially perpendicular to the anterior-posterior direction A-P. The third end 22 is spaced from the fourth end 24 along a medial direction M, while the fourth end 24 is spaced from the third end 22 along a lateral direction L that is opposite the medial direction M. It is to be appreciated that the medial direction M and the lateral direction L are each mono-directional components of the medial lateral direction M-L, which is bi-directional.

One of the medial and lateral ends 22, 24 can be spaced from the other of the medial and lateral ends 22, 24 along a third direction, which can also be referred to herein as the cranial-caudal direction C-C, which is substantially perpendicular to both of the anterior-posterior direction A-P and the medial-lateral direction M-L. It is to be appreciated that the cranial-caudal direction C-C is bi-directional, and consists of a cranial direction CR and a caudal direction CA, which are mono-directional are opposite each other.

Figure 2:
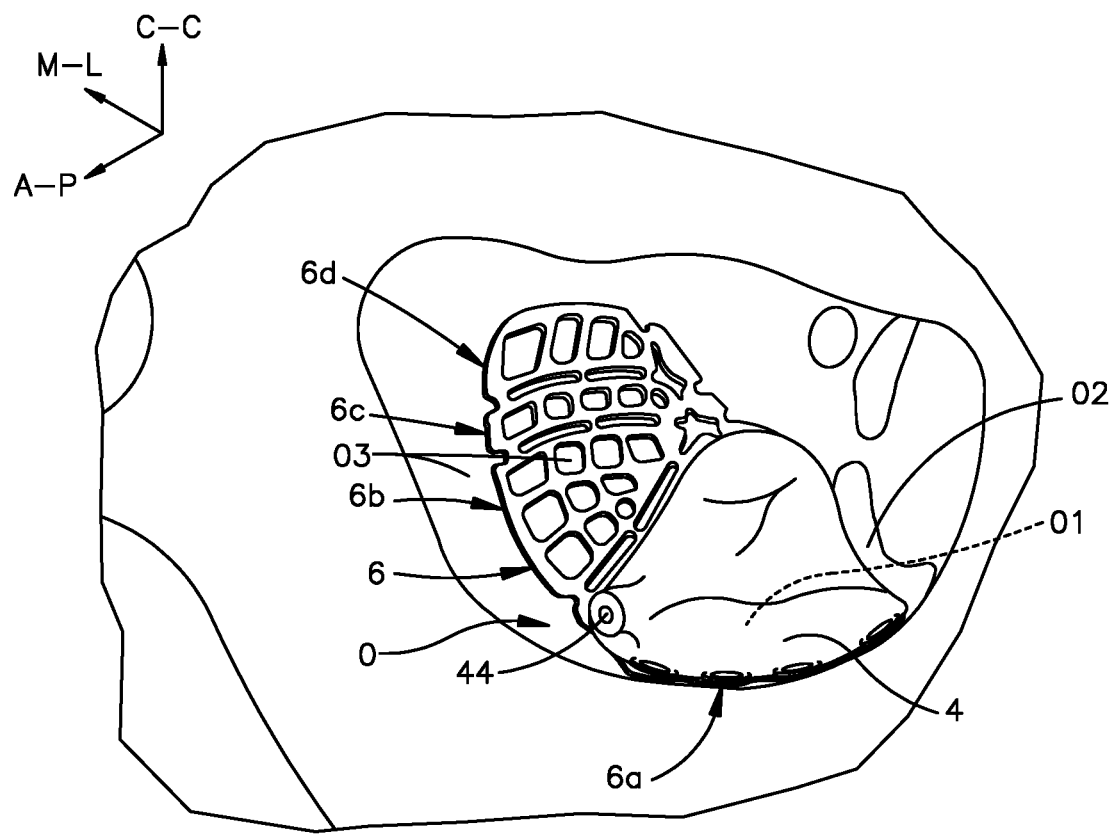
FIG. 2 is a perspective view of the inflatable orbital implant illustrated in FIG. 1 shown implanted onto a target orbit, according to an embodiment of the present disclosure.

The plate 6 can define a plurality of portions that are configured to overlay various portions of the orbit O. In one non-limiting example embodiment, the plate 6 can include a first plate portion 6a at the third end 22, a second plate portion 6b extending from the first plate portion 6a toward the fourth end 24, a third plate portion 6c extending from the second plate portion 6b toward the fourth end 24, and a fourth plate portion 6d extending from the third plate portion 6c to the fourth end 24. In the present example embodiment shown in FIG. 2, the first plate portion 6a can be configured to overlay at least a portion of the floor O1 of the orbit (also referred to herein as the "orbital floor" or simply the "floor"), such as a portion of the floor O1 medial of the orbital fissure O2 and including at least a portion of the orbital surface of the maxilla, by way of a non-limiting example. The first plate portion 6a can also optionally be configured to overlay at least a portion of the orbital process of the palatine bone, and/or at least a portion of the orbital surface of the ethmoid bone, and/or at least a portion of the lacrimal bone, for example. The second, third, and fourth plate portions 6b-d can be configured to progressively extend upwardly along the medial wall O3 of the orbit in the cranial direction CR. By way of a non-limiting example, the second plate portion 6b can be configured to overlay at least a portion of the lacrimal bone, and can optionally also be configured to overlay at least a portion of the orbital surface of the ethmoid bone. The third plate portion 6c, for example, can be configured to overlay the lacrimal bone, and can optionally also be configured to overlay at least a portion of the orbital surface of the ethmoid bone. The fourth plate portion 6d, for example, can be configured to overlay a portion of the orbital surface of the frontal bone. It is to be appreciated that the foregoing description of the plate 6 and orbit O engagements are provided as one non-limiting example of the plate 6 geometry. Accordingly, each plate portions 6a-d can be configured to overlay respective portions of the orbital structure O other than those respective portions described above. It is to be appreciated that, in addition to overlaying respective portions of the orbital structure O, the plate portions 6a-d can also be configured to integrate with the respective portions of the underlying orbital structure O1. For example, the exterior surface 10 can be configured for receiving boney ingrowth, as described in more detail below. It is also to be appreciated that one or more and up to all of the plate portions 6a-d can define a portion of the anterior region A1. It is also to be appreciated that one or more and up to all of the plate portions 6a-d can define a portion of the posterior region P1. Stated differently, one or both of the anterior region A1 and the posterior region P1 of the plate 6 can extend along one or more and up to all of the plate portions 6a-d. Moreover, it is to be appreciated that the plate 6 can optionally include more portions in addition to portions 6a-d. Alternatively, the plate 6 can include fewer than portions 6a-d, such as only one, two, or three of portions 6a-d.

Figure 3:
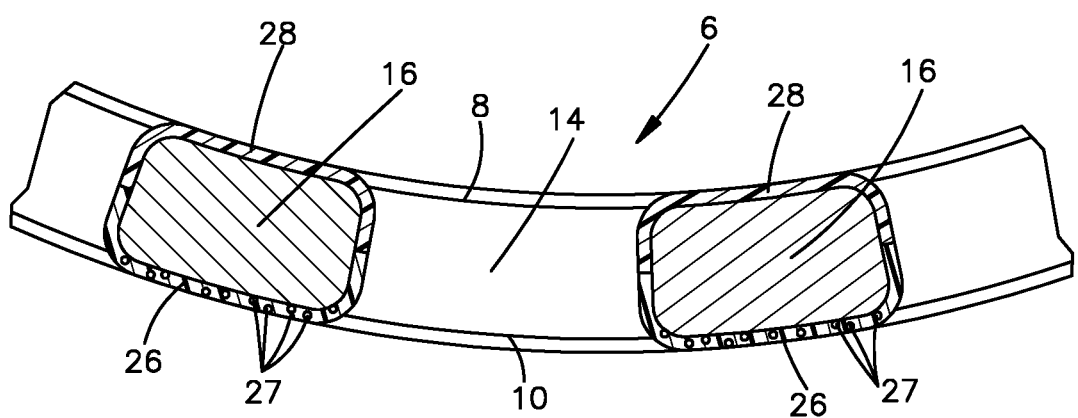
FIG. 3 is a sectional view of a portion of the plate illustrated in FIG. 1 with the inflatable bladder omitted for illustrative purposes, according to an embodiment of the present disclosure.

Referring now to FIG. 3, various portions and up to an entirety of the plate 6 can be adapted to provide the plate 6 with certain characteristics. For example, at least a portion of the plate 6, particularly the exterior surface 10 and optionally also plate surfaces within the apertures 14, can be configured to facilitate boney ingrowth into the plate 6. For example, as shown in FIG. 3, the exterior surface 10 and optionally portions of the plate surfaces within the apertures 14 (particularly those portions of the aperture surfaces that are adjacent the exterior surface 10) can be coated with a coating 26 having pores 27 for receiving boney ingrowth. Thus, the coating 26 can be referred to as a "porous" coating. One non-limiting example of such a coating 26 is a porous polyethylene coating, although other porous coatings are within the scope of the present disclosure. The interior surface 8 of the plate 6 can also have a layer of material 28 disposed thereon for influencing interaction between the plate 6 and the bladder 4. For example, the layer of material 28 (which can also be referred to as a "coating") can include an adhesive for bonding the bladder 4 to the interior surface 8 of the plate 6. In other embodiments, however, it can be desirable to prevent adhesion between the bladder 4 and the interior surface 8 of the plate 6. In such embodiments, the layer of material 28 can include a lower friction material, such as a lubricant, which can be a gel, for example. Alternatively, the interior surface 8 of the plate 6 can be configured to prevent or at least reduce adhesion between the plate 6 and the bladder 4 by being smooth. In such embodiments, the interior surface 8 can undergo a finishing process, such as a polishing process, reducing the surface finish roughness of the interior surface 8. In further embodiments, either or both of coatings 26 and 28 can extend across or "bridge" one or more and up to all of the apertures 14. In yet other embodiments, at least a portion of the plate 6 and up to an entirety of the plate 6 can be embedded within a material, which can be a polymeric material, such as polyethylene, by way of non-limiting example. It is to be appreciated that in embodiments where the entire plate 6 is embedded within a material, the resulting plate construct can be devoid of apertures.

Referring again to FIGS. 1 and 2, the plate 6 can be pre-contoured or pre-shaped to match the geometry of the underlying orbital structure of a patient. The plate 6 can be pre-contoured or pre-shaped to match a generic orbital geometry, or can also be pre-contoured or pre-shaped to match the orbital geometry of a particular patient (i.e., a "patient-specific" orbital geometry) using various techniques, including the techniques more fully described in U.S. Pat. No. 8,281,638, issued on Oct. 9, 2012, and entitled "METHOD AND APPARATUS FOR PRODUCING A PLANAR IMPLANT FOR HUMAN OR ANIMAL BODY" (hereinafter referred to as "the '638 Reference"), the entire disclosure of which is incorporated by reference into this application.

The plate 6 can also include one or more severable portions 7 that are configured to allow a physician to sever one or more plate portions 6a-d from the plate 6. For example, the plate 6 can include a first severable portion 7 between the first and second plate portions 6a, 6b; a second severable portion 7 between the second and third plate portions 6b, 6c; and a third severable portion 7 between the third and fourth plate portions 6c, 6d. The plate 6 can also include additional severable portions 7, such as in the posterior regions P1 of one or more of the first, second, third, and fourth plate portions 6a-d. By way of non-limiting examples, a fourth severable portion 7 can be located in the posterior region P1 of the first plate portion 6a, a fifth severable portion 7 can be located in the posterior region P1 of one of the second and third plate portions 6b, 6c, and a sixth severable portion 7 can be located in the posterior region P1 of the fourth plate portion 6d. The severable portions 7 allow the physician to sever various portions of the plate 6 as needed to adapt the plate 6 to the particular portions of the orbit to be supported, as more fully described in U.S. Pat. No. 7,662,155, issued Feb. 16, 2010, and entitled "IMPLANT FOR USE AS REPLACEMENT OF AN ORBITA BOTTOM" (hereinafter referred to as "the '155 Reference"), the entire disclosure of which is incorporated by reference into this application.

The plate 6 can include one or more fixation structures, such as fixation holes 30 that extend from the interior surface 8 to the exterior surface 10, for receiving complimentary anchoring members, such as bone screws 32, for affixing or otherwise anchoring the plate 6 to the underlying anatomical structure of the orbit O, also referred to herein as the "underlying orbital structure." In the illustrated embodiment, the plate 6 includes a plurality of fixation holes 30 in the anterior region A1 of the first plate portion 6a, such as at the anterior end 18. Each fixation hole 30 is configured to receive a bone screw 32 or other type of bone anchor. It is to be appreciated that the plate 6 described above can be configured similarly to the MATRIX ORBITAL™ Preformed Orbital Plate manufactured by DePuy Synthes Products, Inc., located in Raynham, Mass. In other embodiments, the plate 6 can be configured to be implanted within the orbit O without being mechanically fastened or anchored to the underlying orbital structure. In such embodiments, the plate 6 can be devoid of fixation structures, such as the fixation holes 30.

The bladder 4 includes a body 34 that can overlay one or more portions of the plate 6. The body 34 defines a first or anterior end 35 and a second or posterior end 36 spaced from each other along the anterior-posterior direction A-P. The body 34 also defines a third or medial end 37 and a fourth or lateral end 38 spaced from each other along the medial-lateral direction M-L. In the illustrated embodiment, the body 34 of the bladder 4 overlies the first plate portion 6a, although other configurations are within the scope of the present disclosure. The bladder body 34 can be manufactured from any suitable biocompatible material including polyurethane, a polycarbonate urethane, a polycarbonate-silicone urethane copolymer, a polyamine, a polyethylene terephthalate, a polycaprolactone, and a medical-grade silicone, by way of non-limiting examples. The bladder 4 includes at least one opening or port 44 located at the anterior end 35 of the bladder body 34.

The bladder 4 can include one or more mounting structures, such as one or more mounting tabs 48, for optionally affixing the bladder 4 to the plate 6. The mounting tabs 48 can also be referred to simply as "mounts," and are preferably located at the anterior end 35 of the bladder body 34. The one or more mounting tabs 48 can each include a fixation structure, such as a fixation hole 49, that is configured to anchor the bladder 4 to the underlying orbital structure O. As shown, one or more of the fixation holes 49 of the bladder 4 can overlay a complimentary one of the fixation holes 30 of the plate 6. In this manner, a single bone screw 32 can be inserted through a fixation hole 49 of the bladder 4 and subsequently through the underlying fixation hole 30 of the plate 6 and subsequently into the underlying orbital structure O, thereby affixing or otherwise anchoring the bladder 4 to the plate 6, as well as affixing both the bladder 4 and the plate 6 to the underlying orbital structure O. It is to be appreciated that in other embodiments the fixation holes 49 of the bladder 4 can be offset from the fixation holes 30 of the plate 6 (or the plate 6 can be devoid of fixation holes 30), thus allowing the bladder 4 to be anchored directly to the underlying orbital structure O. In yet other embodiments, the bladder 4 can be implanted so as to overlay the plate 6 without being mechanically fastened or anchored to the plate 6 or to the underlying orbital structure O. In such embodiments, the bladder 4 can be devoid of mounting structures, such as the mounting tabs 48 and fixation holes 49. In such embodiments, the physician may opt to rely on the anatomical structure surrounding the implant 2 to maintain the implant 2 in the desired position in the orbit O.

The bladder 4 includes a first surface 50 that is configured to engage the eyeball E, such as by underlying and supporting the eyeball E, for example, and an opposed second surface 52 that is configured to face the plate 6 and the underlying orbital structure O. The bladder 4 is preferably shaped or otherwise configured so that the first surface 50 cradles or otherwise conforms to the geometry of the eyeball E, at least when the bladder 4 is inflated. The second surface 52 of the bladder 4 can optionally include one or more mounting elements for securing the bladder 4 to the plate 6. For example, such mounting elements can include one or more protrusions 54 configured to extend within one or more of the apertures 14 of the plate 6.

Figure 4A:
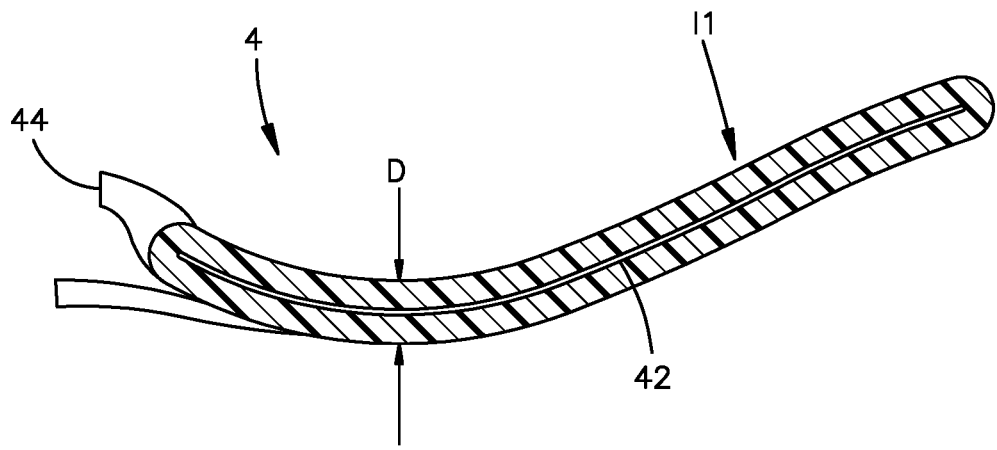
FIG. 4A is a sectional side elevation view of the bladder illustrated in FIG. 1, shown in an uninflated or deflated configuration, according to an embodiment of the present disclosure.
Figure 4B:
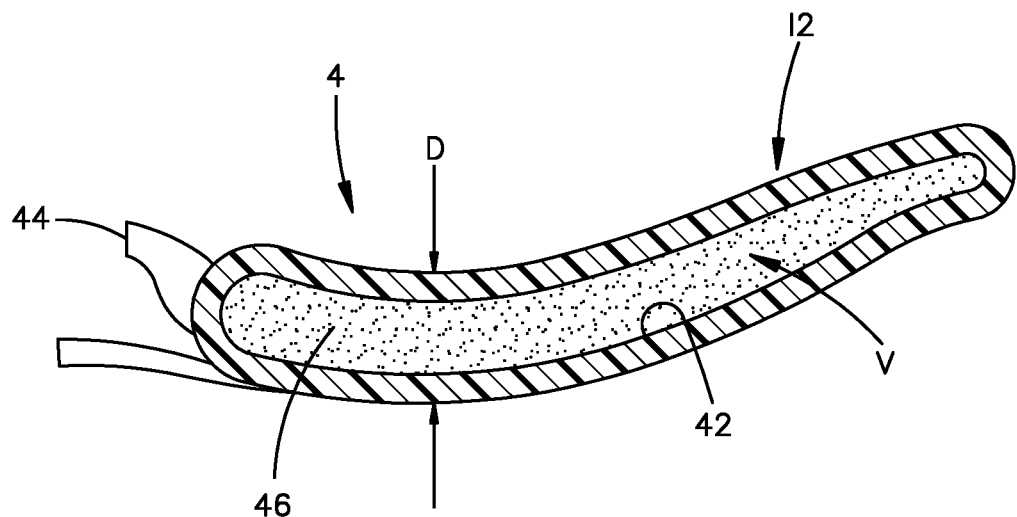
FIG. 4B is a sectional side elevation view of the bladder illustrated in FIG. 1, shown in an inflated configuration, according to an embodiment of the present disclosure.

Referring now to FIGS. 4A and 4B, the bladder 4 defines at least one enclosed, inflatable compartment 42 that defines an interior volume V of space and is in fluid communication with the port 44. The compartment 42 can define the first surface 50, which can be said to be an outer surface of the compartment 42. The compartment 42 is configured to hold a fill material 46 in the interior volume V. It is to be appreciated that the amount of fill material 46 within the compartment 42 determines the interior volume V, and thus also an inflation level of the compartment 42 and thus also of the bladder 4. For example, the bladder can be manipulated between a first or uninflated configuration I1, as shown in FIG. 4A, and a second or inflated configuration I2, as shown in FIG. 4B. Thus, a distance D between the first and second surfaces 50, 52 of the bladder 4 can be adjusted by inflating or deflating the bladder 4. The uninflated configuration I1 can optionally coincide with when the compartment 42 is substantially devoid of the fill material 46. In such embodiments, the interior volume V can be substantially zero in the uninflated configuration I1, although in other embodiments the compartment 42 can define a positive interior volume V when no fill material 46 resides therein.

The fill material 46 can be injected into and/or removed from the compartment 42 through the port 44, thereby adjusting the interior volume V and thus an inflation level of the compartment 42. Thus, it can be said that the interior volume V is adjustable responsive to both injection of the fill material 46 into the compartment 42 through the port 44 as well as removal of fill material 46 from the compartment 42 through the port 44. In this manner, the physician can reposition an eyeball E as needed (see FIG. 5) by adjusting the interior volume V (i.e., by injecting or removing fill material 46 through the port 44). The fill material 46 can be any suitable biocompatible material capable of injection into the compartment 42, such as, by way of non-limiting examples: air, water, a saline solution, a hydrogel, a polyvinyl alcohol, a sodium polyacrylate, an acrylate polymer, a methyl-methacrylate, a copolymer with an abundance of hydrophilic groups, p-vinyl pyrollidone, polyethyleneimine, a polycarbonate urethane (PCU), PCU-silicone copolymer, silicone or other non-resorbable pure or elastic copolymer (for example, PCU's silicone end group modified PUs, RTV curing siloxane based elastomers). In some embodiments, the fill material can be an injectable powder. In the present embodiment, the implant 2 includes a single compartment 42 in communication with a single port 44, although other embodiments involving multiple compartments 42 in communication with multiple respective ports 44 are described below.

Figure 5:
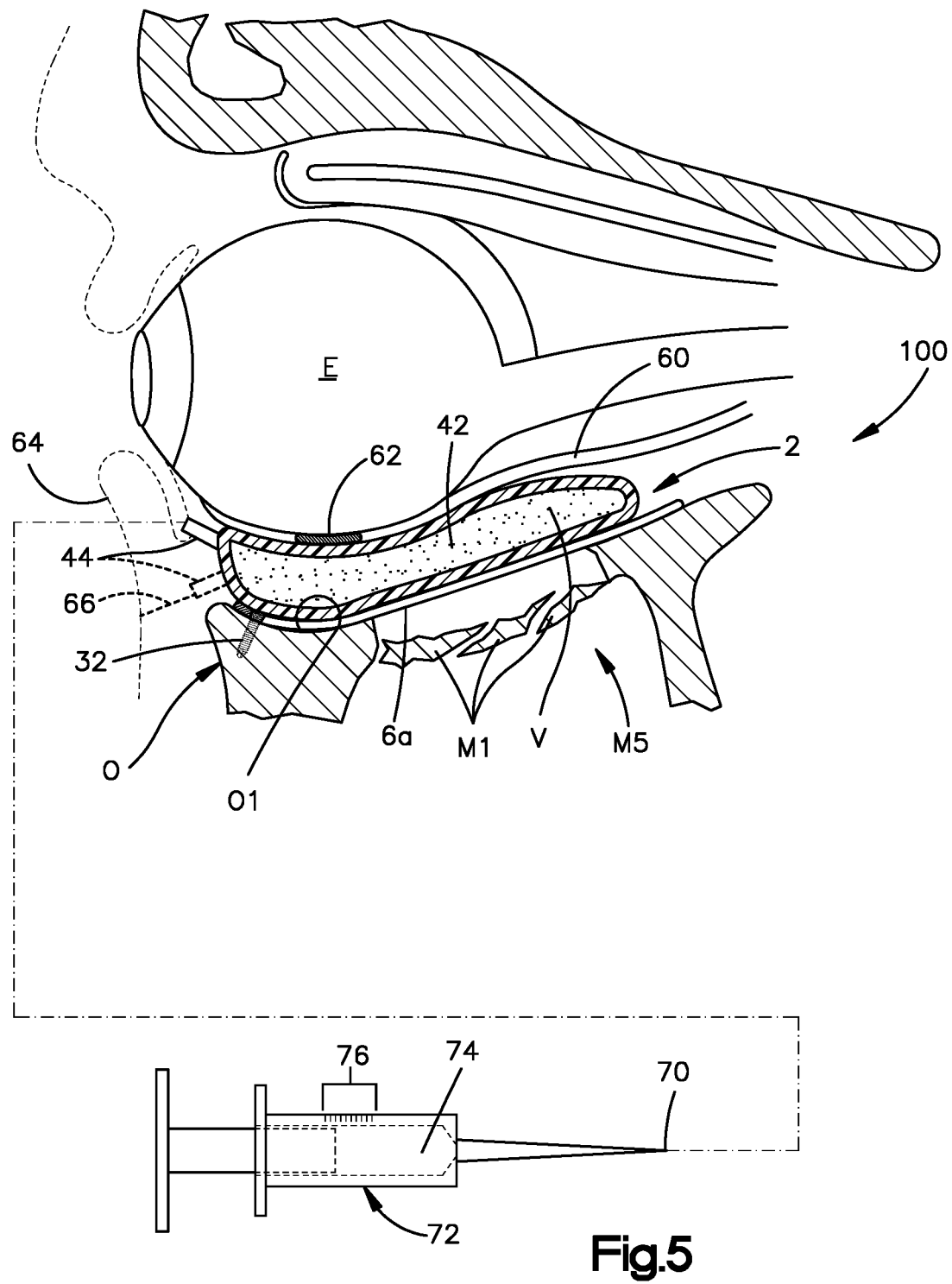
FIG. 5 is a side elevation, partial sectional view of the implant illustrated in FIG. 2 implanted within an orbit of a patient, according to an embodiment of the present disclosure.

Referring now to FIG. 5, the bladder 4 is configured to be implanted, together with the plate 6, within the orbit O such that the bladder 4 is positioned between the eyeball E and the underlying orbital structure O. Particularly, after implantation, the bladder 4 supports the associated eyeball E, while the plate 6 supports the bladder 4. Stated differently, the orbital implant 2 is configured so that, once implanted, the bladder 4 is disposed between the eyeball E and the plate 6, and the plate is disposed between the bladder 4 and the underlying orbital structure O, such as the orbital floor O1, as shown in the present example. Thus, by adjusting the inflation level of the compartment 42, the physician can adjust the distance D between the first and second surfaces 50, 52 of the bladder 4, and thus also the distance between the eyeball E and the underlying orbital structure O.

During an orbital floor O1 reconstruction according to an example embodiment of the present disclosure, a physician can implant the first plate portion 6a and the bladder 4 within the orbit O by anchoring the first plate portion 6a and bladder 4 to a target portion of the underlying orbital structure O by inserting bone screws 32 through the fixation holes 30, 49 and driving the bone screws 32 into the underlying maxilla and/or zygomatic bone. Upon implantation, the first plate portion 6a and the bladder 4 can extend in the posterior direction P to a posterior portion of the orbital surface of the maxilla or even to the orbital surface of the ethmoid bone and/or the orbital process of the palatine bone. In this manner, the bladder 4 can be disposed between the eyeball E and orbital structure O, preferably along a direction in which it is desired to reposition the eyeball E. In the illustrated example, the bladder 4 can be disposed between the orbital floor O1 and the underside (i.e., the inferior side) of the eyeball E, whereby the first surface 50 of the bladder 4 can engage the eyeball E. As mentioned above, such engagement can include cradling or otherwise supporting the eyeball E, which can also include cradling or otherwise supporting the inferior rectus muscle 60 and the inferior oblique muscle 62, as well as adipose tissue (i.e., fat)

between the underside of the eyeball E and the orbital floor O1. It is to be appreciated that the bladder 4 can be uninflated, partially inflated, or even fully inflated during implantation, according to the needs of the patient. In instances where a portion of the orbital floor O1 has collapsed, such as with an "orbital blowout" fracture of the floor O1 resulting in maxillary fragments M1 falling within the maxillary sinus MS, for example, and/or where the floor O1 is comminuted, the plate 6 can optionally be pre-shaped to reside within the vacated portion of the floor O1. In some instances, it may be preferred that the plate 6 resides lower with respect to the floor O1 relative to prior art orbital implants, such as to provide additional room for the bladder 4. It is to be appreciated that the apertures 14 in the plate 6 can allow blood to drain from the orbit O into the maxillary sinus MS.

Post-operatively, such as when the patient awakes from the orbital reconstruction in the clinic, the physician can check the patient's vision and eye alignment. If misalignment of the eyes is detected and/or the patient experiences diplopia, the physician (or a technician) can inflate or deflate the bladder 4 as needed, by injecting fill material 46 through the port 44 and into the compartment 42 or removing fill material from the compartment through the port 44, respectively, until alignment of the eyes is restored and/or diplopia is cured. In this manner, instant or virtually instant results for avoiding or curing diplopia can be obtained, based on positive patient feedback, can be obtained with the implants 2 disclosed herein. Moreover, if the eyeball E supported by the implant 2 subsequent drops out of alignments, such as a result of tissue necrosis (e.g., necrosis of fat cells) between the bladder 4 and the eyeball E, the eyeball E can be repositioned back into alignment by further inflating the bladder 4 using the techniques described above, even years after the implantation procedure. Thus, the implants 2 disclosed herein can provide for repeated re-alignment of the eyeball E as needed throughout the life of the implant 2.

The port 44 can be configured to extend from the compartment 42 in the anterior direction A so as to be accessible underneath the lower eyelid 64. In such embodiments, the physician can access the port 44 by simply manually pulling the lower eyelid down, thereby exposing the port 44, and inserting a fluid coupling, such as an injection needle 70, into the port 44. In other embodiments, the port 44 can be located beneath or behind soft tissue (or at least so that soft tissue will grow over the port 44 post-operatively). In one example of such an embodiment, the port 44 can be located proximate the base of the lower eyelid 64 and the superior surface of the maxilla, as shown in dashed lines in FIG. 5. In such an embodiment, the port 44 can be accessible through an incision at the base of the eyelid, such as an infraorbital incision 66, or alternatively the port 44 can be targeted through the base of the lower eyelid with the injection needle 70.

To adjust the inflation level, the physician can inject and/or withdraw the fill material 46 into and/or from the compartment 42 via an injection device 72 that is configured to communicate (i.e., flow) a quantity of the fill material 46 through the port 44. The injection device 72 includes, or is in fluid communication with, a fluid supply or reservoir 74 of the fill material 46. As shown, the injection device 72 can be a syringe carrying the injection needle 70. The injection device 72 can include visual indicia, such as hatch marks 76 disposed over the fluid supply 74 and coinciding with predetermined inflation levels of the compartment 42. However, other types of injection devices 72 are within the scope of the present disclosure, such as, for example, metering pumps, such as diaphragm pumps, peristaltic pumps, and the like, that are capable of dispensing predetermined quantities or "doses" of fill material 46, which quantities can coincide with predetermined levels of inflation of the bladder 4. It is to be appreciated that in other embodiments, the compartment 42, the injection device 72, and/or the fluid supply 74 can include a pressure sensing device for sensing, calculating, approximating, or otherwise determining the pressure within the compartment 42. In such embodiments, the fluid supply 74 and/or the injection device 72 can be configured to allow the physician to specifically adjust the pressure within the compartment 42, such as to alleviate discomfort, by way of non-limiting example. The implant 2 and the injection device 72, including the reservoir 74, can comprise an orbital implantation system 100. It is to be appreciated that the features depicted in FIG. 5, including the syringe 72, are not drawn to scale.

Figure 6:
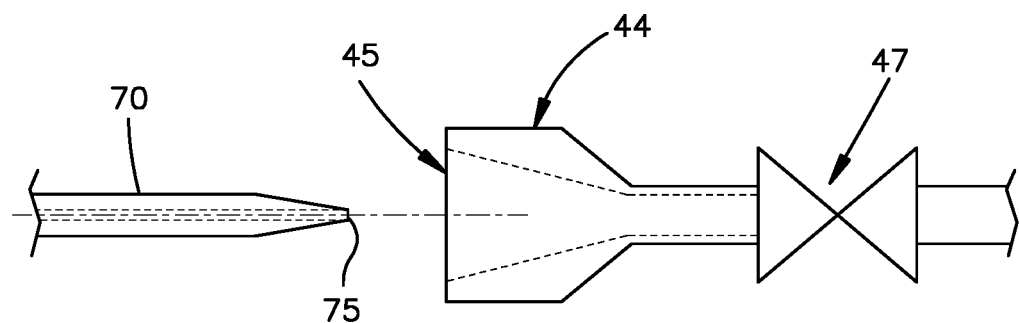
FIG. 6 is a side plan view of a fluid coupling between a fluid injection device and a port of an inflatable bladder, such as the bladder shown in FIG. 1, according to an embodiment of the present disclosure.
Figure 7:
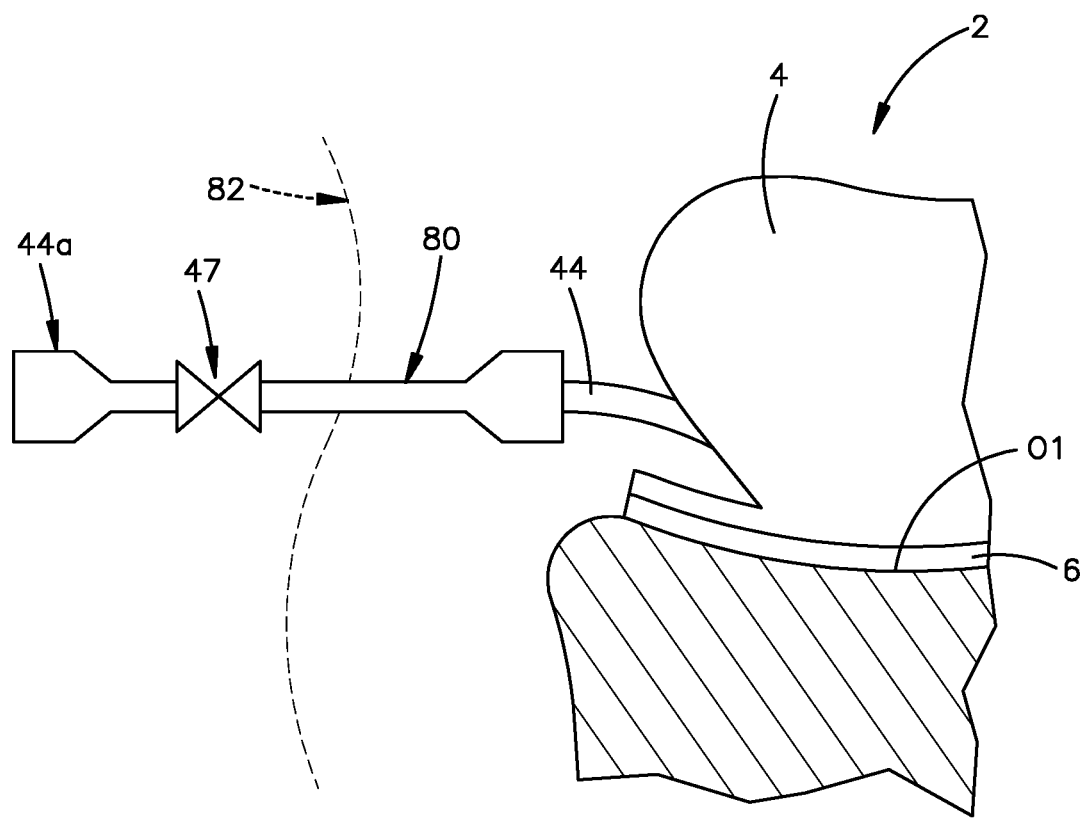
FIG. 7 is a plan view of a port extension for ex vivo injection of a fill material for inflating the inflatable bladder, according to an embodiment of the present disclosure.

Referring now to FIG. 6, in some embodiments, the port 44 can include a funnel-shaped opening 45 configured to guide the injection needle into the port 44. The port 44 can also include a valve element 47 configured to prevent fill material 46 from exiting the compartment 42 through the port 44 inadvertently. The valve element 47 can be a self-sealing valve, such as a self-sealing polymeric membrane configured to be penetrated by the distal tip 75 of the injection needle 70, and then to collapse or otherwise close in upon itself in a sealing manner after the needle 70 is withdrawn. It is to be appreciated that other valve types are within the scope of the present disclosure. The valve element 47 can also be configured to release or "bleed" fill material 47 from the compartment 42 through the port 44. As shown in FIG. 7, in some embodiments, the implant 2 can include an extension 80, such as a cannula, coupled to the port 44 and extending to a second port 44a located external of the patient 82. The extension 80 can include a valve element 47 external of the patient 82. In such embodiments, the bladder 4 can be inflated and/or deflated via the extension 80, which can then be removed after the bladder 4 has reached the desired inflation level. It is to be appreciated that the extension 80 can also be employed in embodiments where the port 44 is accessible without penetrating the patient's tissue, such as below the lower eyelid 64 as shown in FIG. 5.

Figure 8:
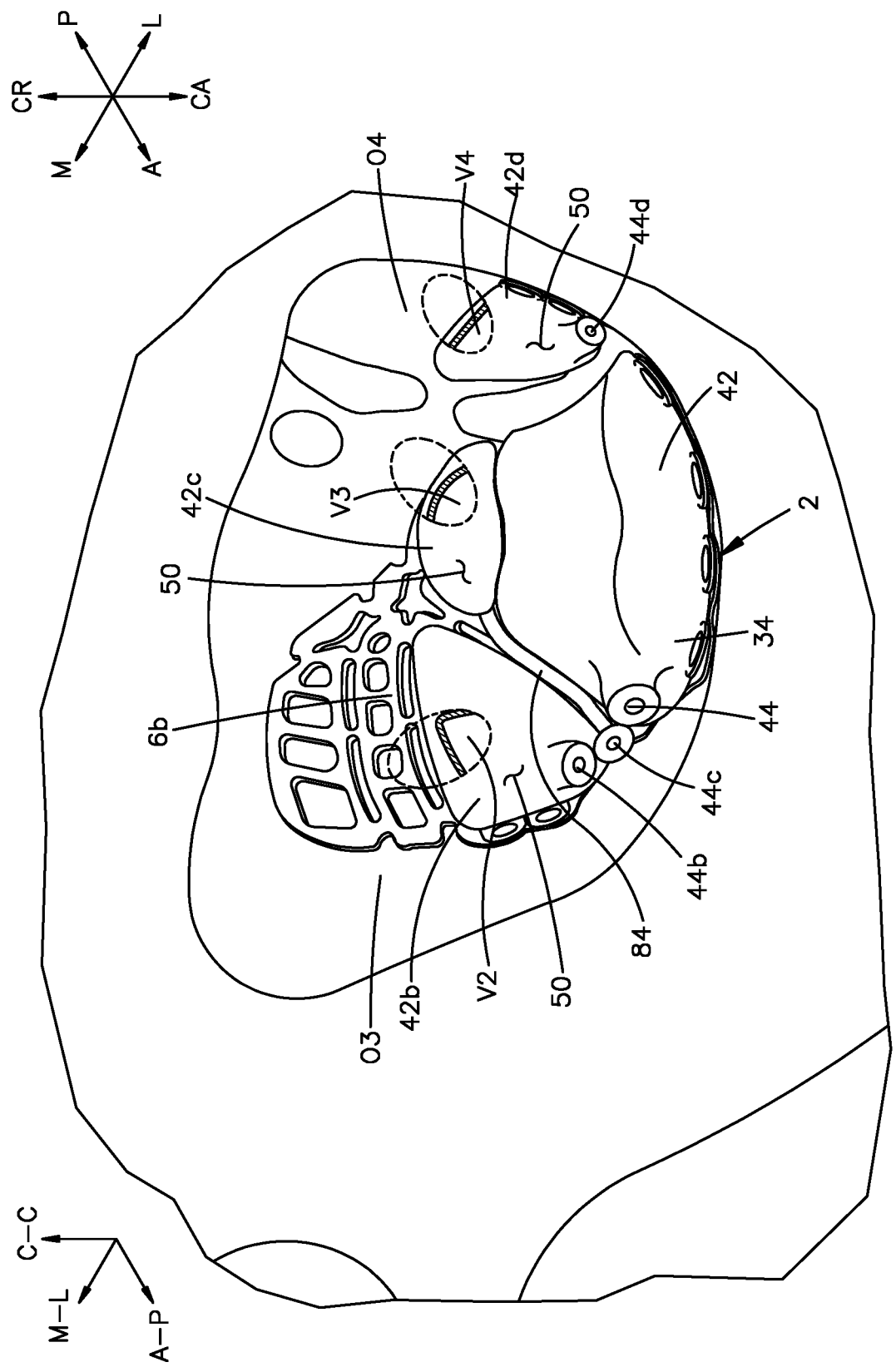
FIG. 8 is a perspective view of an inflatable orbital implant having a plurality of inflatable compartments, shown implanted onto a target orbit, according to an embodiment of the present disclosure.

Referring now to FIG. 8, in additional embodiments, the implant 2 can include a plurality of inflatable compartments 42. Accordingly, the compartment 42 can be referred to as a first compartment, and the implant 2 can include a second inflatable compartment 42b for providing additional repositioning capability for the eyeball E. For example, the second compartment 42b can be configured to overlay another portion of the plate 6, such as the second plate portion 6b so as to also overlay at least a portion of the medial wall O3. In this manner, the second compartment 42b can be configured to reposition the eyeball E at least partially along the medial-lateral direction M-L, particularly by biasing the eyeball E in the lateral direction L (or at least in a direction having a directional component in the lateral direction L). Preferably, the second compartment 42b is configured so as to be disposed at a location inferior of the medial rectus muscle so as not to interfere with its operation (or at least to reduce interference with its operation).

The second compartment 42b can be configured similarly to the first compartment 42; accordingly, the second compartment 42b can include the features of the first compartment 42 described above. Accordingly, the second compartment 42b defines a second internal volume V2 and is in fluid communication with a second port 44b located at the anterior end 35. Moreover, the inflation level of the second compartment 42b can be adjusted by injecting and/or withdrawing fill material 46 into and/or from the second compartment 42b through the second port 44b via an injection device 72. As with the first compartment 42, the second compartment 42b defines a first surface 50 that is configured to engage the eyeball E, which engagement can include cradling or otherwise conforming to the geometry of the eyeball, at least when the second compartment 42b is inflated. Preferably, the internal volumes V1, V2 of the first and second compartments 42, 42b are isolated from each other (i.e., not in fluid communication with each other) so that the inflation levels of the first and second compartments 42, 42b can be adjusted independently to reposition the eyeball E as needed. It is to be appreciated that in other embodiments, however, that the internal volumes V1, V2 can be in fluid communication with each other.

The implant 2 can also include a third inflatable compartment 42c for providing additional repositioning capability for the eyeball E. For example, the third compartment 42c can be configured to overlay the posterior portion P1 of the first plate portion 6a, or at least a portion thereof, and thus can be configured to overlay a posterior portion of the orbital floor O1. In this manner, the third compartment 42c can be configured to reposition the eyeball E at least partially along anterior-posterior direction A-P, particularly by biasing the eyeball E in the anterior direction A, or at least in a direction having a directional component in the anterior direction A, responsive to inflation of the third compartment 42c. It is to be appreciated that the third compartment 42c can be configured to reposition the eyeball E in the posterior direction P, or at least in a direction having a directional component in the posterior direction P, responsive to deflation of the third compartment 42c. In such embodiments that include the third compartment 42c, the first compartment 42 can be shorter along the anterior-posterior direction A-P than it is in the embodiment described above with reference to FIGS. 1 through 5; moreover, the third compartment 42c can be positioned posterior of the first compartment 42.

The third compartment 42b can be configured similarly to the first compartment 42; accordingly, the third compartment 42c can include the features of the first compartment 42 described above. Accordingly, the third compartment 42c defines a third internal volume V3 and is in fluid communication with a third port 44c located at the anterior end 35. A tube 84 can extend between and thereby provide fluid communication between the third port 44c and the third compartment 42c. Similar to the manner described above, the inflation level of the third compartment 42c can be adjusted by injecting and/or withdrawing fill material 46 into and/or from the third compartment 42c through the third port 44c via an injection device 72. The third compartment 42c defines a first surface 50 that is configured to engage a posterior portion of the eyeball E, which engagement can include cradling or otherwise conforming to the geometry of the eyeball, at least when the third compartment 42c is inflated. Preferably, the internal volume V3 of the third compartment 42c is isolated from the internal volumes V1, V2 of the first and second compartments 42, 42b so that the inflation level of the third compartment 42c can be adjusted independently to reposition the eyeball E as needed. For example, to reposition the eyeball in the anterior direction A, the physician can: increase the inflation level of the third compartment 42c and maintain the inflation level in the first compartment 42; decrease the inflation level of the first compartment 42 and increase the inflation level of the third compartment 42c; or increase the inflation levels of both the first and third compartments 42, 42c. It is to be appreciated that the internal volume V3 of the third compartment 42c can alternatively be in fluid communication with one or both of V1 and V2 in other embodiments.

The implant 2 can also include a fourth inflatable compartment 42d for providing additional repositioning capability for the eyeball E, such as at least partially along the medial-lateral direction M-L, particularly by biasing the eyeball E in the medial direction M (or at least in a direction having a directional component in the medial direction M). The fourth compartment 42d can be configured to overlay a portion of the lateral wall O4 of the orbit O, such as the orbital surface of the zygomatic bone. Preferably, the fourth compartment 42d is configured so as to be disposed at a location inferior of the lateral rectus muscle, so as not to interfere with its operation (or at least to reduce interference with its operation). The fourth compartment 42d can overlay a fifth plate portion 6e that overlies the portion of the lateral wall O4. The fifth plate portion 6e can be connected to and/or monolithic with the first plate portion 6a. Alternatively, the fifth plate portion 6e can be a second plate separate from plate 6.

The fourth compartment 42d can be configured similarly to the first compartment 42; accordingly, the fourth compartment 42d can include the features of the first compartment 42 described above. Accordingly, the fourth compartment 42d defines a fourth internal volume V4 and is in fluid communication with a fourth port 44d located at the anterior end 35. Moreover, the inflation level of the fourth compartment 42d can be adjusted by injecting and/or withdrawing fill material 46 into and/or from the fourth compartment 42d through the fourth port 44d via an injection device 72. As with the first compartment 42, the fourth compartment 42d defines a first surface 50 that is configured to engage the eyeball E, which engagement can include cradling or otherwise conforming to the geometry of the eyeball, at least when the fourth compartment 42d is inflated. Preferably, the internal volume V4 of the fourth compartment 42d is isolated from the internal volumes V, V2, V3 of the first, second, and third compartments 42, 42b, 42c so that the inflation level of the fourth compartment 42d can be adjusted independently to reposition the eyeball E as needed. It is to be appreciated, however, that in other embodiments the internal volume V4 of the fourth compartment 42d can be in fluid communication with one or more and up to each of the internal volumes V1, V2, V3 of the first, second, and third compartments 42, 42b, 42c.

It is to be appreciated that the implant 2 can be configured to employ any combination of the first, second, third, and fourth compartments 42, 42b, 42c, 42d, including only one of the first, second, third, or fourth compartments 42, 42b, 42c, 42d, and up to all of the first, second, third, and fourth compartments 42, 42b, 42c, 42d, as desired for the particular needs of the patient. In embodiments comprising multiple compartments 42, the respective ports 44 can be configured to be proximate one another, at least after implantation, for ease of access with the injection device 72.

It is also to be appreciated that any one of the first, second, third, and fourth compartments 42, 42b, 42c, 42d can be comprised of a bladder body 34 that is separate from and non-monolithic with that of any one other and up to all others of the compartments 42, 42b, 42c, 42d. In such embodiments, each compartment 42, 42b, 42c, 42d that is comprised of a separate bladder body 34 can be said to be a part of a distinct or separate bladder 4. Thus, in such embodiments, the implant 2 can be characterized as a bladder assembly that includes a plurality of bladders 4 each comprising at least one inflatable compartment 42. In such embodiments, at least some of the bladders can be implanted through separate incisions in the patient. In other embodiments, two or more and up to all of the compartments 42, 42b, 42c, 42d can be formed of a single, monolithic bladder body 34. It is also to be appreciated that, although four compartments 42, 42b, 42c, 42d are shown in FIG. 8, the implant 2 can include more than four compartments.

Figure 9:
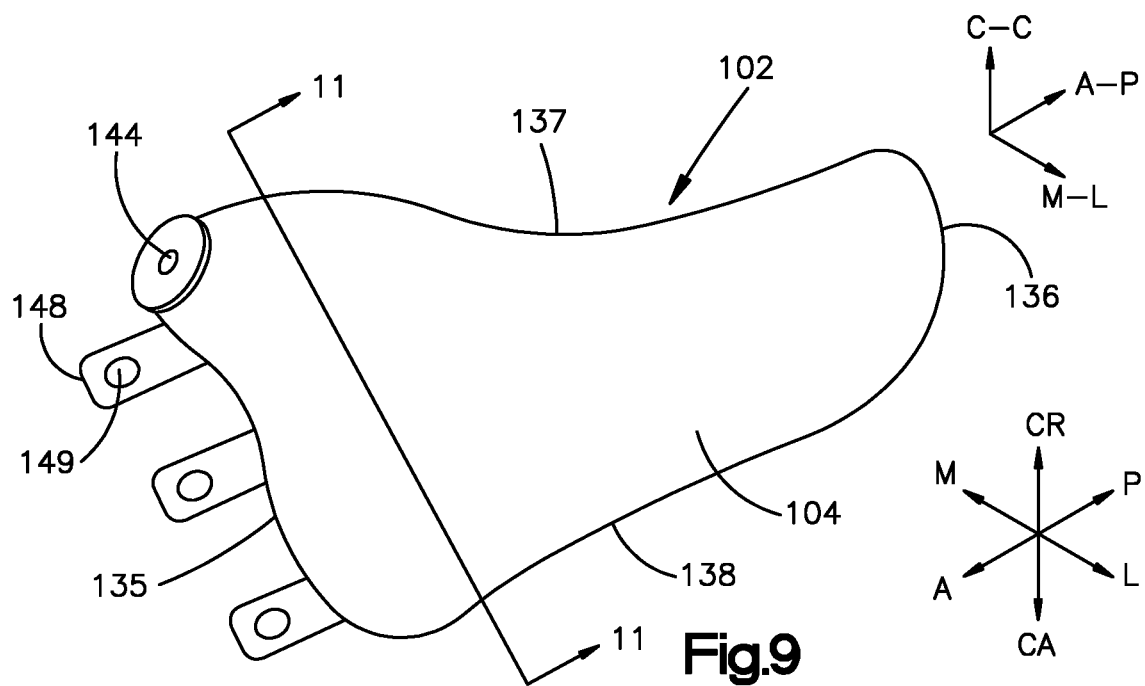
FIG. 9 is a perspective view of an inflatable orbital implant that includes an inflatable bladder for use without an underlying plate, according to an embodiment of the present disclosure.
Figure 10:
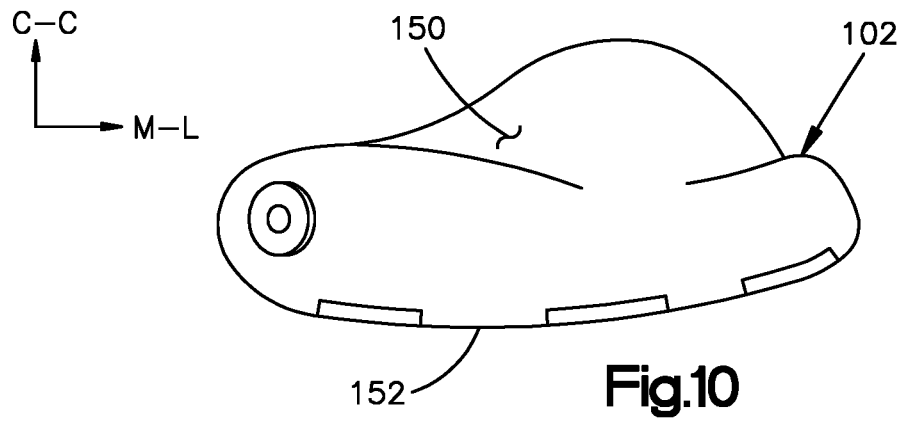
FIG. 10 is a front elevation view of the inflatable orbital implant illustrated in FIG. 9.
Figure 11:
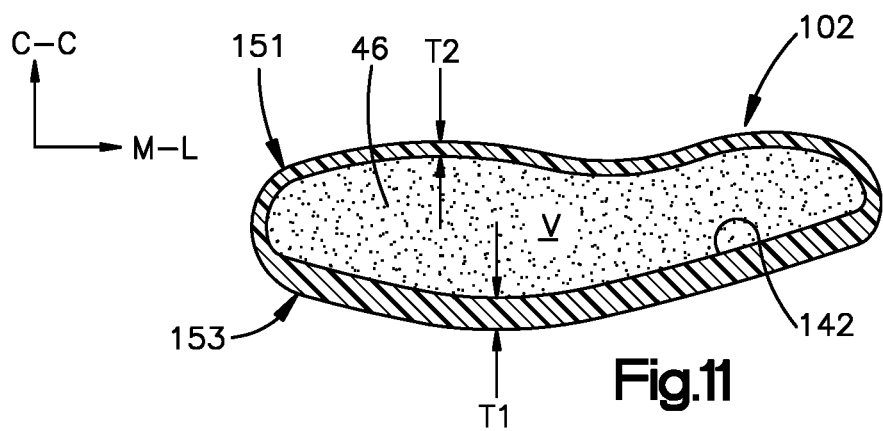
FIG. 11 is an end sectional view of the inflatable orbital implant taken along section line 11-11 illustrated in FIG. 9, according to an embodiment of the present disclosure.

Referring now to FIGS. 9 through 11, in other embodiments, an orbital implant 102 can include an inflatable bladder 104 that is configured to reposition an eyeball E without the use of an underlying support plate, such as plate 6. Accordingly, the bladder 104 of the present embodiment can be referred to as a "stand-alone" bladder. The bladder 104 of the present embodiments can be configured similarly to the bladders 4 of any of the embodiments described above with reference to FIGS. 1 through 8. The bladder 104 includes a body 134 that is configured to overlay a portion of the orbital structure O, particularly the orbital floor O1, the medial wall O3, and/or the lateral wall O4, for example. In this manner, the bladder 104 can be implanted between the eyeball E and the orbital structure O1. The body 134 defines a first or anterior end 135 and a second or posterior end 136 spaced from each other along the anterior-posterior direction A-P. The body 134 also defines a third or medial end 137 and a fourth or lateral end 138 spaced from each other along the medial-lateral direction M-L. The bladder 104 includes at least one enclosed, inflatable compartment 142 that defines an internal volume V configured to hold the fill material 46. The bladder 104 includes at least one opening or port 144 that is located at the anterior end 135 and is in fluid communication with the internal volume V, whereby the inflation level of the compartment 142 can be adjusted by injecting and/or withdrawing fill material through the port 144, as described above. Thus, by adjusting the inflation level of the compartment 142, the physician can adjust a distance between the first and second surfaces 150, 152, and thus also the distance between the eyeball E and the underlying orbital structure O, thereby repositioning the eyeball E relative to the orbit O as needed.

An inner portion 151 of the bladder 104 can define the first surface 150 and an exterior portion 153 of the bladder 104 can define the second surface 152. As shown in FIG. 11, the exterior portion 153 can be define a cross-sectional thickness T1 that is optionally greater than a cross-sectional thickness T2 of the inner portion 151. In this manner, the increased thickness T1 of the exterior portion 153 can provide increased rigidity for supporting the implant 102 over the underlying anatomical structure O (and thus increased support for the eyeball E), as well as enhanced shape retention of the second surface 152 (and thus of the bladder 104). The anterior end 135 of the bladder 104 can include one or more mounting structures, such as mounting tabs 148 defining associated fixation holes 149 that are configured to receive complimentary anchoring members, such as bone screws 32, for anchoring the bladder 104 to the underlying orbital structure O, similar to the manner described above. The bladder 104 includes a first surface 150 that is configured to engage the eyeball E, such as by underlying and supporting the eyeball E, and an opposed second surface 152 that is configured to engage the underlying orbital structure O. As described above, the bladder 104 can be configured so that the first surface 150 cradles or otherwise conforms to the geometry of the eyeball E, at least when the bladder 104 is inflated. The second surface 152 of the bladder 104 can optionally include one or more affixation elements for affixing with the underlying orbital structure O, such as protrusions (similar to the protrusions 54 described above), recesses, adhesives, and/or pores for receiving boney ingrowth, by way of non-limiting example. In yet other embodiments, the bladder 104 can be implanted so as to overlay the orbital structure O without being mechanically fastened or anchored thereto. In such embodiments, the bladder 104 can be devoid of mounting structures, such as the mounting tabs 148 and fixation holes 149, and can also be devoid of recesses, adhesives, and/or pores for receiving boney ingrowth. In such embodiments, the physician may opt to rely on the surrounding anatomical structure to maintain the bladder 104 in the desired position within the orbit O.

During an orbital floor O1 reconstruction with the stand-alone bladder 104, according to an example of the present disclosure, the bladder 104 can be implanted within the orbit O by disposing the bladder 104 adjacent a target portion of the orbital structure O, preferably so as to be aligned with the eyeball E along a direction in which it is desired to reposition the eyeball E. Optionally, anchoring members, such as bone screws 32, can be inserted through the fixation holes 149 and driven into the underlying orbital structure O so as to anchor the bladder 104 to the underlying orbital structure O and adjacent the eyeball E. As described above, the physician can check the patient's vision and eye alignment post-operatively, and can inflate or deflate the bladder 104 as needed by injecting or removing fill material 46 through the port 144 until alignment of the eyes is restored and/or diplopia is cured. The port 144 can be located on the bladder 104 similarly as described above. Additionally, the port 144 can optionally be coupled to an extension 80 that extends externally from the patient, as described above with reference to FIG. 7.

It is to be appreciated that the stand-alone bladder 104 can include a plurality of bladders and inflatable compartments 142, which can be configured similarly to any of the embodiments of the compartments 42, 42b, 42c, 42d described above with reference to FIG. 8, for repositioning the eyeball along multiple directions. Moreover, it is also to be appreciated that the bladders 4 according to any of the embodiments described above with reference to FIGS. 1, 2, 4, 5, 7, and 8 can optionally be employed as a stand-alone bladder or stand-alone bladders (i.e., can be implanted to the orbital structure O without a plate underneath).

It is further to be appreciated that the bladders 4, 104 described herein are also capable of being inflated with a hardenable or curable fill material.

Although the disclosure has been described in detail, it should be understood that various changes, substitutions, and alterations can be made herein without departing from the spirit and scope of the invention as defined by the appended claims. It is also to be appreciated that one or more elements, features, components, and/or structures of one of the embodiments can be employed in other embodiments. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. An inflatable orbital implant, comprising:
a bladder configured to be implanted between an orbit and an eyeball of a patient, the bladder defining at least one port and at least one compartment in fluid communication with each other, the at least one compartment defining an interior volume, the at least one compartment configured to hold a fill material such that the interior volume is adjustable responsive to 1) injection of fill material into the at least one compartment through the at least one port to inflate the at least one compartment, and 2) removal of fill material from the at least one compartment through the at least one port to deflate the at least one compartment, wherein the adjustment of the interior volume is configured to reposition the eyeball;

a reservoir of fill material located externally of the patient; and an injection device in fluid communication with the reservoir and configured to communicate a quantity of the fill material though the at least one port so as to adjust the interior volume of the at least one compartment, wherein the bladder defines one or more fixation structures each defining a hole configured to receive an anchor for affixing the bladder to one or more bones of the orbit, wherein the at least one port comprises a first port, a second port, and a third port; and wherein the at least one compartment comprises:

a first compartment in fluid communication with the first port, the first compartment configured to be disposed between the eyeball and a floor of the orbit and overlaying the floor of the orbit, wherein the first compartment is configured to reposition the eyeball along a cranial-caudal direction during inflation and deflation of the first compartment;

a second compartment in fluid communication with the second port, the second compartment configured to be disposed between the eyeball and a medial wall of the orbit, wherein the second compartment is configured to reposition the eyeball along a medial-lateral direction during inflation and deflation of the second compartment; and a third compartment in fluid communication with the third port, at least a portion of the third compartment being spaced from the first and second compartments in a posterior direction, wherein the third compartment is configured to reposition the eyeball along an anterior-posterior direction during inflation and deflation of the third compartment, and wherein the first, second, and third compartments are discrete from each other.

2. The inflatable orbital implant of claim 1, wherein the first compartment is configured to overlay an anterior portion of the floor, and the third compartment is configured to overlay a posterior portion of the floor.

* * * * *